United States Patent [19]

Tokizane et al.

[11] Patent Number: 4,811,217

[45] Date of Patent: Mar. 7, 1989

[54] METHOD OF STORING AND SEARCHING CHEMICAL STRUCTURE DATA

[75] Inventors: Soichi Tokizane; Hideaki Chihara, both of Tokyo, Japan

[73] Assignee: Japan Association For International Chemical Information, Tokyo, Japan

[21] Appl. No.: 844,016

[22] Filed: Mar. 25, 1986

[30] Foreign Application Priority Data

Mar. 29, 1985 [JP] Japan ................................ 60-63283

[51] Int. Cl.⁴ .............................................. G06F 15/20
[52] U.S. Cl. ..................................... 364/300; 364/900
[58] Field of Search ... 364/200 MS File, 900 MS File, 364/300

[56] References Cited

U.S. PATENT DOCUMENTS

| | | | |
|---|---|---|---|
| 4,085,443 | 4/1978 | Dubois et al. ........................ | 364/900 |
| 4,473,890 | 9/1984 | Araki .................................. | 364/900 |
| 4,642,762 | 2/1987 | Fisanick ............................. | 364/300 |

FOREIGN PATENT DOCUMENTS 0090895 10/1983 European Pat. Off. .

OTHER PUBLICATIONS

A. Von Scholley, "A Relaxation Algorithm for Generic Chemical Structure Screening", J. Chem. Inf. Comp. Sci., 1984(24), 235-241.
Lynch, M. F. et al., "Comp. Storage and Retrieval of Generic Chem. Structures in Patents, Part 1", J. Chem. Inf. Comp. Sci., 1981(21), 148-150.
Barnard, J. M. et al., "Comp. Storage and Retrieval of Generic Chem. Structures in Patents, Part 4", J. Chem. Inf. Comp. Sci., 1982(22), pp. 160-164.
Welford, S. M. et al., "Comp. Storage and Retrieval of Generic Chem. Structures in Patents, Part 5", J. Chem. Inf. Comp. Sci., 1984(24), pp. 57-66.
"The Automation of Structural Group Contribution Methods in the Estimation of Physical Properties", Journal of Chemical Documentation, vol. 8, No. 2, May 1968, Neil Jochelson, C. Michael Mohr, and Robert C. Reid.
"On Some Clustering Techniques", IBM Journal, Jan. 1964, R. E. Bonner.
"A Computer Program for Generation of Constitutionally Isomeric Structural Formulas", J. Chem. Inf. Comput. Sci., 1984, 24, 220-229, Hidetsugu Abe, Tohru Okuyama, Iwao Fujiwara, and Shin-Ichi Sasaki.
"Simulation and Evaluation of Chemical Synthesis, Computer Representation and Manipulation of Stereochemistry", Journal of the American Chemical Society, 96:15, July 24, 1974, W. Todd Wipke and Thomas M. Dyott.
"Chemical Substance Retrieval System for Searching Generic Representations, 1, A Prototype System for the Gazetted List of Existing Chemical Substances of Japan", J. Chem. Inf. Comput. Sci., 1983, 23, 109-117, Yoshihiro Kudo and Hideaki Chihara.
"Chemical Information System", edited by J. E. Ash and E. Hyde, Ellis Horwood Ltd., 1975 (book), pp. vi-309.

Primary Examiner—Gareth D. Shaw
Assistant Examiner—Rebecca L. Adams
Attorney, Agent, or Firm—Wenderoth, Lind & Ponack

[57] ABSTRACT

Chemical structure data containing generic representation of component atoms in a storage device is searched by finding a match between a query structure and a stored candidate structure by mathematically comparing attribute data of chemical units of a query structure and attribute data of chemical unit of a stored candidate structure, where attribute data represent chemical characteristics of chemical units of those structures.

5 Claims, 6 Drawing Sheets

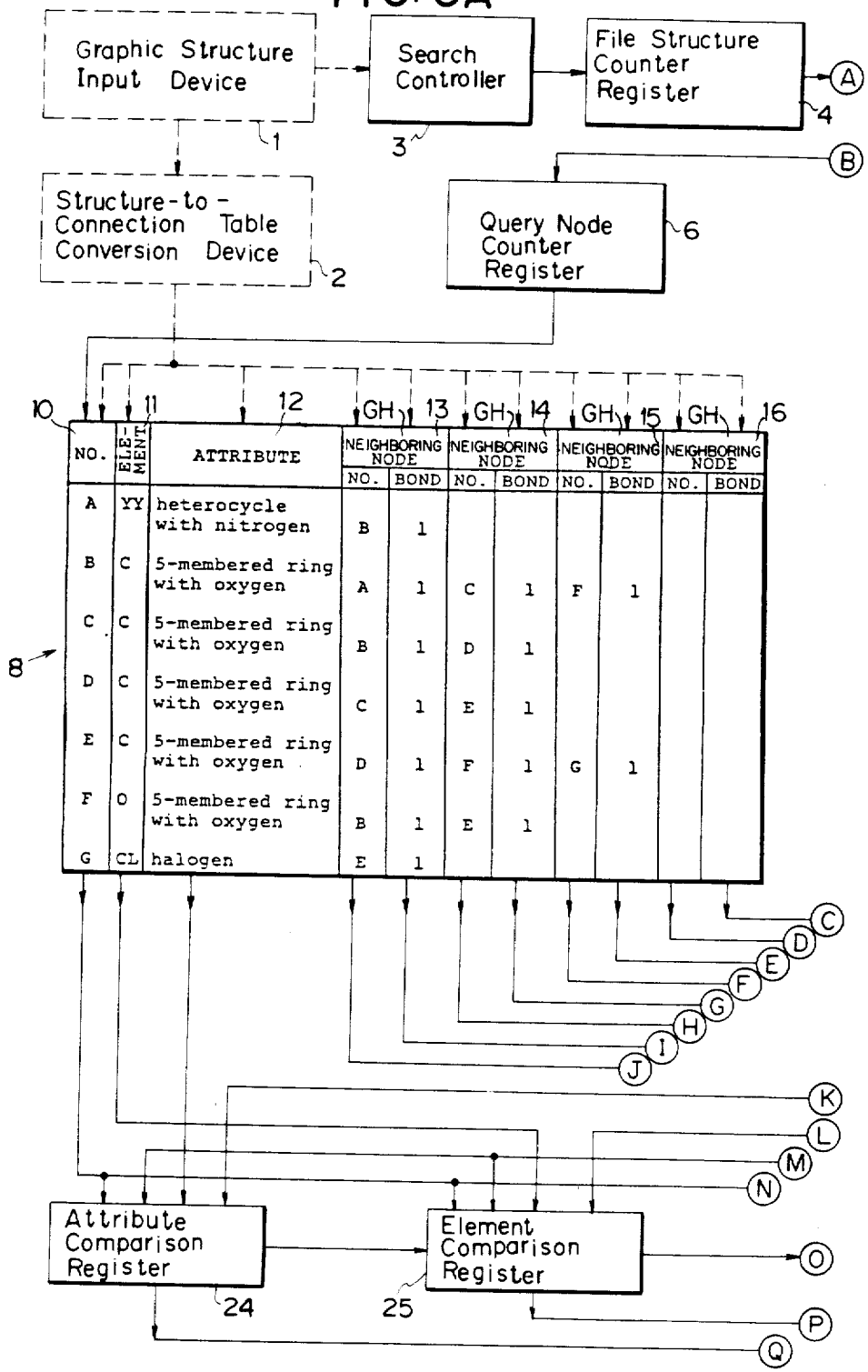

METHOD OF STORING AND SEARCHING CHEMICAL STRUCTURE DATA

BACKGROUND OF THE INVENTION

1. Field of the Invention

This invention relates to a method of storing chemical structure data in a storage device and searching said chemical structure data using a query chemical structure by examining the match or analogy between the query structure and the stored structure data.

2. Description of the Prior Art

Recently various information including patent information is more and more handled by computers. Textual data, which consist of alphanumerics, such as patent claim information or technical information are now stored as a database and specific pieces of information are easily retrieved by searching the database. In the textual database, keywords are picked up from each piece of information, generally called a record, and those keywords are sorted alphabetically in the database as an inverted file. A search is conducted by combining a record list of eack keyword using the Boolean operation with AND, OR, or NOT logical operators. The basic idea of this method was introduced early in 1960's. The first computer system using this method was introduced in the 1970's in the United States. Most of the current online information retrieval systems use this type of textual data retrieval method.

On the other hand, storage and retrieval of chemical structure information, which is a graphic data in nature, was not so easy to achieve as that of textual data. Handling of chemical substance data is discussed in a book, "Chemical Information System", edited by J. E. Ash and E. Hyde, Ellis Horwood Ltd., 1975. A related U.S. Pat. is No. 4,085,443 by Araki. It was only early in the 1980's when the chemical structure storage and retrieval systems were available commercially. An inverted file which is used to handle textual information is not applicable to graphic data such as chemical structure data. Rather it is necessary to compare atoms and bonds of a query chemical structure with those of each chemical structure stored in a database to find a match between those structures. In order to do this comparison, it is necessary to create and keep so-called connection tables for all query and file structures. Since this comparison requires tracking atom connections one by one, it is usually called an iterative search. The iterative search consumes much computer time and affects the overall search time considerably, and it is necessary to minimize the number of candidate file structures to which iterative searches are to be conducted by screening out most of the "unwanted" structures. The screening is achieved by checking for the presence or absence of particular chemical characteristics called screens requested by the query structure. For example, if the query structure contains a nitrogen atom, any file structures which does not have nitrogen atoms will be screened out. In a current commercial system, screens are created automatically by a computer, when a query structure was created through an interactive session on a remote graphic terminal.

Thus, the current chemical structure search systems can handle specifically defined structures which are ususally found in technical journals. On the other hand, a generic expression of a chemical structure is widely used in patent claims to widen the coverage of those claims. Specific examples of such generic expressions are:

Alkyl groups with C1-C5 chain.
    Aromatic rings (i.e., benzene or naphthalene)
    Heterocyclic (i.e., rings containing one or more non-carbon atoms) groups with a ring size of 5 or 6.

The generic expression often covers thousands or millions of specific chemical structures, and allows one to expand the scope of a claim without specifically identifying each structure. Since chemical substances themselves are patentable in most countries, it is very important to store and search the generic chemical structures. The current status of the handling of generic chemical structures is discussed thoroughly in the following references.

(1) "Computer Storage and Retrieval of Generic Chemical Structures in Patents. 1. Introduction and General Strategy" by M. F. Lynch, S. M. Welford, and J. M. Bernard, J. Chem. Inf. Comput. Sci., 1981, (21), 148–150.

(2) "Computer Storage and Retrieval of Generic Shemical Structures in Patents. 2. GENSAL, a Formal language for the Description of Generic Chemical Structures" by J. M. Barnard, M. F. Lynch, and S. M. Welford, J. Chem. Inf. Comput. Sci., 1981, (21), 151–161.

(3) "Computer Storage and Retrieval of Generic Chemical Structures in Patents. 3. Chemical Grammars and their Role in the Manipulation of Chemical Structures" by S. M. Welford, M. F. Lynch, and J. M. Barnard, J. Chem. Inf. Comput. Sci., 1981, (21), 157–163.

(4) "Computer Storage and Retrieval of Generic Structures in Chemical Patents. 4. An Extended Connection Table Representation for Generic Structures" by J. M. Barnard, M. F. Lynch, and S. M. Welford, J. Chem. Inf. Comput. Sci., 1982, (22), 160–164.

(5) "Chemical Substance Retrieval System for Searching Generic Representations. 1. A Prototype System for the Gazetted List of Existing Chemical Substances of Japan" by Y. Kudo and H. Chihara, J. Chem. Inf. Comput. Sci., 1983, (23), 109–117.

(6) "Computer Storage and Retrieval of Generic Chemical Structures in Patents. 5. Algorithmic Generation of Fragment Descriptors for Generic Structure Screening" by S. M. Welford, M. F. Lynch, and J. M. Barnard, J. Chem. Inf. Comput. Sci., 1984 (24), 57–66.

(7) "Computer Storage and Retrieval of Generic Chemical Structures in Patents. 6. An Interpreter Program for the Generic Structure Description Language GENSAL" by J. W. Barnard, M. F. Lynch, and S. M. Welford, J. Chem. Inf. Comput. Sci., 1984 (24), 66–71.

(8) "A Relaxation Algorithm for Generic Chemical Structure Screening" by A. Von Scholley, J. Chem. Inf. Comput. Sci., 1984 (24) 235–241.

Because of its complexity, no system can handle generic chemical structures successfully until now, except that two approach were made to solve the problem partially.

(APPROACH A)

One approach is to store specific structures expressed by the generic structures. Practically a database containing structure information of substances specifically identified in patent examples is widely used. One example is the Registry File of CAS ONLINE. But patent examples usually describe only a portion of the generic structures in a claim, and thus it is not usually true that the combination of all chemical structures in the examples corresponds to the claimed generic expression. It is certainly not practical to expand generic structures into component specific structures, since the number of specific structures derived from one generic structure easily explodes to millions. For example, an expression C4–C5 alkyl group represents 12 specific alkyl radicals. If a generic structure contains three of these expressions, the combination will result in $12 \times 12 \times 12$ or 1728 specific structures.

(APPROACH B)

The other approach is to define codes for various chemically significant units, such as rings, chains and functional groups, and search the structure via those codes like keywords of textual detabases. The examples are the World Patent Index of Derwent or Comprehensive Database of IFI. In this approach, the expression C4–C5 alkyl group may be coded into two keywords, C4 and C5. Thus even a very complex generic structure can be coded fairly simply. One shortcoming of this approach is that a searcher has to know the coding rule and use the necessary codes explicitly. For example, in searching for a propyl group, one has to specify keywords both PROPYL and C3 ALKYL. But a bigger problem is that the coding system cannot express the connection between the chemical units successfully. This results in large number of irrevelant answers, which are usually called noise. Often more than 90% of the answer structures are noise. Another disadvantage is that since the file has no connection tables, or exact representation of chemical structures, it is unable to search by structures, as one can do in the system based on specific connection tables. Thus the searcher needs to learn how to use the code system to code a query structure effectively. Apparently, this prevents the system from being used widely.

SUMMARY OF THE INVENTION

Either one of the two current approaches described above does not fulfill the needs of the generic structure searching. In addition, in the true generic structure search sytem, a query structure itself may have many generic expressions as well as the structures stored in a database. This type of search, namely generic structure searching using a generic structure query, has been considered almost impossible.

Among many problems in developing a generic structure search system based on chemical structures rather than code systems, the biggest one is how to represent such generic structure units as alkyl, heterocyclic, etc., usually described as textual information in the patent disclosure, in a structure connection table as searchable information. In comparing a query structure with a file structure, it is necessary to find a match between non-identical expressions. For example, we find a match when the query requires the presence of a C1–C5 alkyl and a file structure has a C4–C7 alkyl, because the component of C4 and C5 of the file structure satisfy the requirement of the query. Also there is a match between a query specifying a nitrogen-containing ring and a file structure containing a six-membered (ring size of six) heterocycle.

The claimed invention is intended to solve the above problems in developing the generic structure search system and to provide it for practical use.

Thus, a method is provided for storing chemical structure data in a storage device and searching said chemical structure data using a query chemical structure by examining the match or analogy between the said query structure with the structure data stored, which comprises:

assigning numbers to each chemical unit of each structure to be stored, storing the numbers of chemical units to which the said chemical unit is chemically connected in a connection table, and storing the attribute data, which describe the chemical characteristics of the said chemical unit, in an attribute table;

then assigning numbers to each chemical unit of the query chemical structure to be used to search the stored chemical structure data, and storing the numbers of chemical units to which the said chemical unit is chemically connected in a connection table, and storing the attribute data, which describe the chemical characteristics of the said chemical unit, in an attribute table;

then examining the match or analogy of the query structure and each stored chemical structure by comparing chemical units of the query chemical structure with the corresponding chemical unit of the stored chemical structure by matching the attributes of the chemical unit of the stored chemical structure and the attributes of the corresponding chemical units of the query structure according to a mathematical condition defined in advance.

BRIEF DESCRIPTION OF THE DRAWINGS

FIGS. 5A–5B together show an apparatus which would operate in accordance with the present invention.

DESCRIPTION OF THE PREFERRED EMBODIMENT

Figure 1:
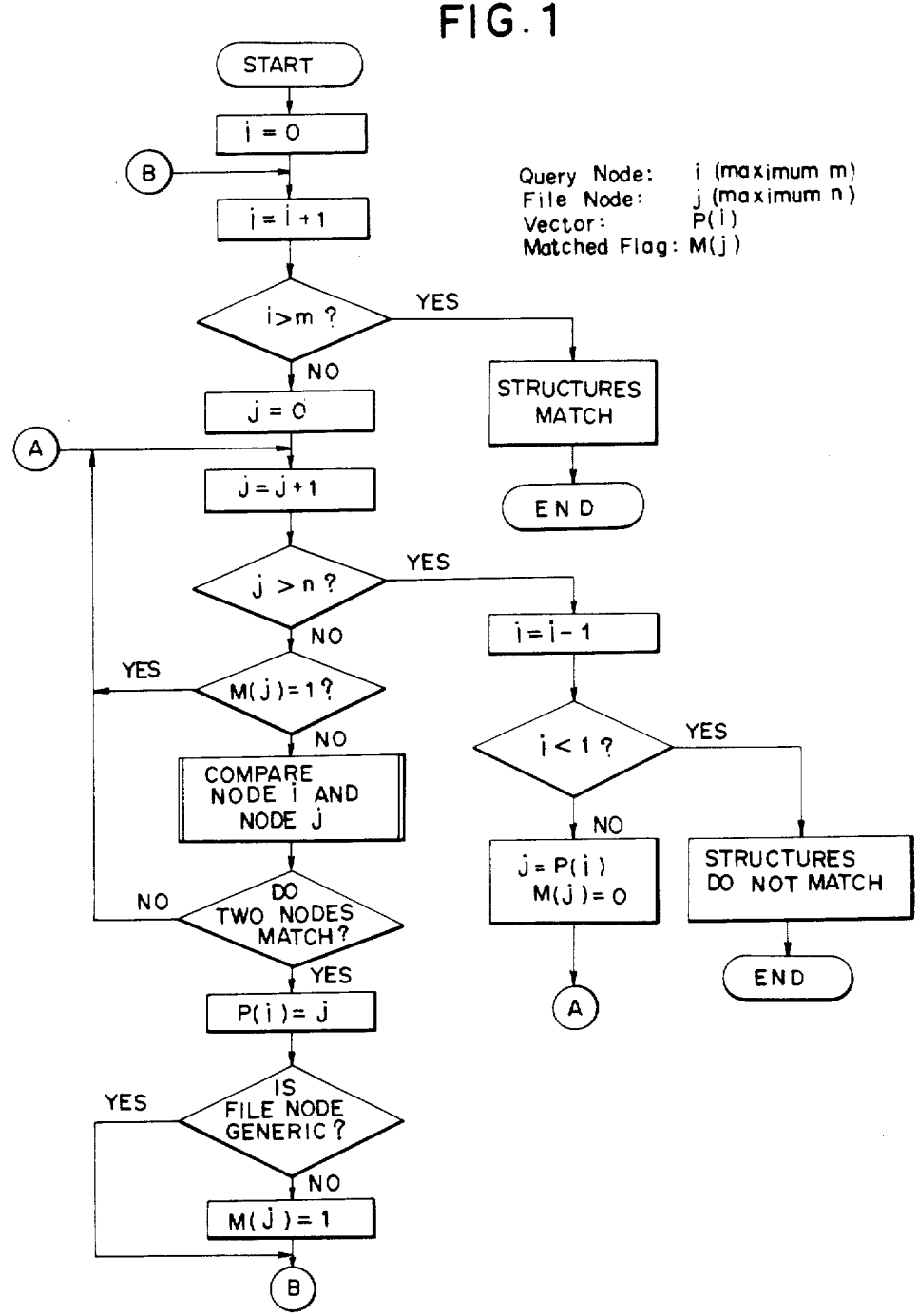
FIG. 1 illustrates a search algorithm based on the connectivity stack method.

The present invention will now be described in detail in conjunction with a preferred mode thereof.

(1) Sample Generic Chemical Structures

The stored structure (Structure 1) is represented by the connection table (Table 1) and the attribute table (Table 2), and the query structure (Structure 2) is represented by the connection table (Table 3) and the attribute table (Table 4).

STRUCTURE 1

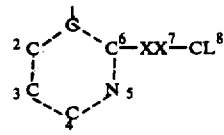

(XX is an oxygen-containing ring system consisting of one or two component rings with the ring size of five or six.)

The search process is described step by step in Table 5 and the chain attribute is described in Table 6.

First, all of the atoms (including generic atoms) except for hydrogen atoms, which will be called nodes hereafter, are numbered at will. In this example, these nodes correspond to the chemical units described earlier.

TABLE 1

| NO. | ELEMENT | ATTRIBUTE | NEIGHBORING NODE NO. | NEIGHBORING NODE BOND | NEIGHBORING NODE NO. | NEIGHBORING NODE BOND | NEIGHBORING NODE NO. | NEIGHBORING NODE BOND | NEIGHBORING NODE NO. | NEIGHBORING NODE BOND |
|---|---|---|---|---|---|---|---|---|---|---|
| 1 | C | 6-membered ring with nitrogen | 2 | 4 | 6 | 4 | | | | |
| 2 | C | 6-membered ring with nitrogen | 1 | 4 | 3 | 4 | | | | |
| 3 | C | 6-membered ring with nitrogen | 2 | 4 | 4 | 4 | | | | |
| 4 | C | 6-membered ring with nitrogen | 3 | 4 | 5 | 4 | | | | |
| 5 | N | 6-membered ring with nitrogen | 4 | 4 | 6 | 4 | | | | |
| 6 | C | 6-membered ring with nitrogen | 1 | 4 | 5 | 4 | 7 | 1 | | |
| 7 | XX | 5- or 6-membered ring with nitrogen | 6 | 1 | 8 | 1 | | | | |
| 8 | CL | halogen | 7 | 1 | | | | | | |

A table is created with each row representing each node of the structure and the first column representing the node number. The second column shows the element type of the node, the third column shows the attribute code of the node, the fourth column shows the number of a node to which the current node is connected, and the fifth column shows the bond value of the connection above. The bond value is coded such that a single bond is represented by 1, double bond, 2, triple bond, 3, aromatic bond, 4. In Structure 1, a single bond is represented by a straight line and an aromatic bond by a broken line. It is important that column 4 and 5 form a pair to describe the connection information. Similarly, the pairs of column 6 and 7, 8 and 9, and 10 and 11 each describe connections of the current node to the other nodes. Although there are only four pairs of the connection information in Table 1 and 3, one may add more columns if more than four connections are expected.

Although attribute data is expressed by words in Tables 1 and 3 to enhance the comprehension, it is usually represented by bit-maps as shown in Tables 2 and 4.

TABLE 2

| | RING ATOM | | | | RING SIZE | | | | RING NUMBER MINIMUM | | | RING NUMBER MAXIMUM | | |
|---|---|---|---|---|---|---|---|---|---|---|---|---|---|---|
| NO. | O | S | N | A | 4 | 5 | 6 | >6 | 1 | 2 | 3 | 1 | 2 | 3 |
| 1 | 0 | 0 | 1 | 0 | 0 | 0 | 1 | 0 | 1 | 0 | 0 | 1 | 1 | 1 |
| 2 | 0 | 0 | 1 | 0 | 0 | 0 | 1 | 0 | 1 | 0 | 0 | 1 | 1 | 1 |
| 3 | 0 | 0 | 1 | 0 | 0 | 0 | 1 | 0 | 1 | 0 | 0 | 1 | 1 | 1 |
| 4 | 0 | 0 | 1 | 0 | 0 | 0 | 1 | 0 | 1 | 0 | 0 | 1 | 1 | 1 |
| 5 | 0 | 0 | 1 | 0 | 0 | 0 | 1 | 0 | 1 | 0 | 0 | 1 | 1 | 1 |
| 6 | 0 | 0 | 1 | 0 | 0 | 0 | 1 | 0 | 1 | 0 | 0 | 1 | 1 | 1 |
| 7 | 1 | 0 | 0 | 0 | 0 | 1 | 1 | 0 | 1 | 1 | 0 | 1 | 1 | 1 |

Thus, pre-defined chemical characteristics of each chemical unit, or node in this example, are assigned a position in the bit-map vector, which is widely used in computer programming. If a particular chemical characteristics exists in the node, the position of the bit-map is filled by the number 1, otherwise it is filled by the number 0. Although there is no limitation in the length of the bit-map, or the number of positions in it, the range may be between 4 to 4096, preferably 8 to 512, to make best use of computer resources. These bit-maps are easily handled by the ordinary electronic computer systems. Thus, the generic node expression in the node 7 of Table 1 is expressed as follows. First a dummy element code XX is put in the row 7, column 2 of Table 1, showing that the node 7 is a generic node. Then, each column (bit-map position) of row 7 of Table 2 is filled with either a 1 or 0 depending on the presence or the absence of the corresponding chemical characteristics. For numeric characteristics, such as the count of carbon atoms, or the number of rings, two sets of columns are usually prepared to represent both the maximum and minimum values. In this context, a minimum value simply means the actual value may not be lower than it, and a maximum value means the actual value may not be larger than it. Thus, in Table 2, when the number of rings is one, the column of minimum value of 1 is filled with 1, and the columns of maximum value of 1, 2 and 3 are filled with 1. When the number of rings is in the range of 1 to 2 as the node 7, the columns corresponding to the minimum value of 1 and 2, and the maximum value of 1, 2 and 3 are filled with 1. The latter case may be interpreted by combining the bit-maps corresponding to the number of rings, 1 and 2, by logical operator OR.

Since only the ring-related attributes are shown in Table 2 to make the explanation simple, the node 8 does not have any attribute here. The important point is that this attribute bit-map is generated for all nodes of the structure regardless of whether or not they are generic. It is convenient to define separate attributes for rings and chains. Although it is very easy to distinguish if a generic node is a ring or a chain in most cases, it may be necessary to divide a structure into two, namely, one with a ring node and one with a chain node, when the distinction is not very clear.

A search is conducted by comparing one by one the nodes of the query structure (Structure 2) with the nodes of the stored structure.

STRUCTURE 2

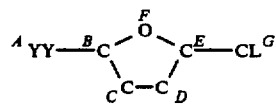

(YY is a nitrogen-containing heterocycle. The number of component rings is unlimited.)

TABLE 3

| NO. | ELE-MENT | ATTRIBUTE | NEIGHBORING NODE | | NEIGHBORING NODE | | NEIGHBORING NODE | | NEIGHBORING NODE | |
|---|---|---|---|---|---|---|---|---|---|---|
| | | | NO. | BOND | NO. | BOND | NO. | BOND | NO. | BOND |
| A | YY | heterocycle with nitrogen | B | 1 | | | | | | |
| B | C | 5-membered ring with oxygen | A | 1 | C | 1 | F | 1 | | |
| C | C | 5-membered ring with oxygen | B | 1 | D | 1 | | | | |
| D | C | 5-membered ring with oxygen | C | 1 | E | 1 | | | | |
| E | C | 5-membered ring with oxygen | D | 1 | F | 1 | G | 1 | | |
| F | O | 5-membered ring with oxygen | B | 1 | E | 1 | | | | |
| G | CL | halogen | E | 1 | | | | | | |

The nodes of the query structure are assigned alphabet values rather than numerals. The generic node A of the query structure is assigned a dummy element value of YY. In the ordinary chemical structure search systems, it is convenient to examine the match of element type first and then the matches of the connection, which consists of the node number of the connecting atom and the bond value. In this invention the matches of attributes are most important. Although the examination steps described in Table 5 show that the element matches precede the attribute match, this order is not critical. It is also possible to eliminate the element matches entirely.

The attributes of the query structure are shown in Table 4. Since the number of rings of the node A is undefined (more than one), only the column of the minimum value of 1 is assigned the number 1. Also no attribute is assigned for the size of the ring.

TABLE 4

| NO. | RING ATOM | | | | RING SIZE | | | | RING NUMBER | | | | | |
|---|---|---|---|---|---|---|---|---|---|---|---|---|---|---|
| | | | | | | | | | MIN-IMUM | | | MAX-IMUM | | |
| | O | S | N | A | 4 | 5 | 6 | >6 | 1 | 2 | 3 | 1 | 2 | 3 |
| A | 0 | 0 | 1 | 0 | 0 | 0 | 0 | 0 | 1 | 0 | 0 | 0 | 0 | 0 |
| B | 1 | 0 | 0 | 0 | 0 | 1 | 0 | 0 | 1 | 0 | 0 | 1 | 1 | 1 |
| C | 1 | 0 | 0 | 0 | 0 | 1 | 0 | 0 | 1 | 0 | 0 | 1 | 1 | 1 |
| D | 1 | 0 | 0 | 0 | 0 | 1 | 0 | 0 | 1 | 0 | 0 | 1 | 1 | 1 |
| E | 1 | 0 | 0 | 0 | 0 | 1 | 0 | 0 | 1 | 0 | 0 | 1 | 1 | 1 |
| F | 1 | 0 | 0 | 0 | 0 | 1 | 0 | 0 | 1 | 0 | 0 | 1 | 1 | 1 |

A match is determined when every column of the attribute bit-map of a stored structure node fulfill the corresponding column of the bit-map of a query structure node, i.e., if a column of the query node is one, then the corresponding column of the stored structure node MUST be one. On the other hand, if the column is zero, the corresponding column of the stored structure node can be either one or zero. It is possible to exchange the value one and zero, depending on the system architecture. It is also possible to define values other than 1 and 0.

When one uses a standard bit-map with values 1 and 0, it is very easy to compare the bit-map of the query structure with the bit-map of the stored structure using a series of logical operations usually available on an electronic computer. An example step is to NOT the bit-map of the stored structure, and then to AND the result with the bit-map of the query structure. If the result of the AND operation is a zero vector, or a bit-map filled with zeros, then the positions of the bit-map of the stored structure correspond to the positions of the bit-map of the query structure. For example, the result of the NOT operation of the bit-map 1 of Table 2 (0010 0010 100 111) is 1101 1101 011 000. When it is ANDed with the bit-map A of Table 4 (0010 0000 100 000), the result is 0000 0000 000 000. Thus, all the chemical characteristics defined on the bit-map A by bits 1 do exist in the bit-map 1. On the other hand, the result of AND operation with the bit-map B (1000 0100 100 111) is 1000 0100 000 000 and is not all-zero. Thus, we know the ring atom O and ring size 4 do not exist in the bit-map 1.

Another alternative may be to compare the attribute columns if one is larger than the other. The invention described here is characteristic in that the comparison is made on some mathematical methods discussed above rather than a simple code or keyword (text) matching.

(2) Search Process

We chose here substructure searching, where a match is successful when a given query structure is logically involved or embedded in a candidate structure. Thus, an examination is over either when all query nodes are matched with corresponding file nodes, or when it is found that such a query-file node correspondence does not exist. All the query nodes should be examined, but not all the file nodes, as long as the above condition is fulfilled.

One may choose searches other than substructure searching. There are several differences which exist between different types of searches in the process described above. But the use of the attribute is valid in any process.

Figure 5B:
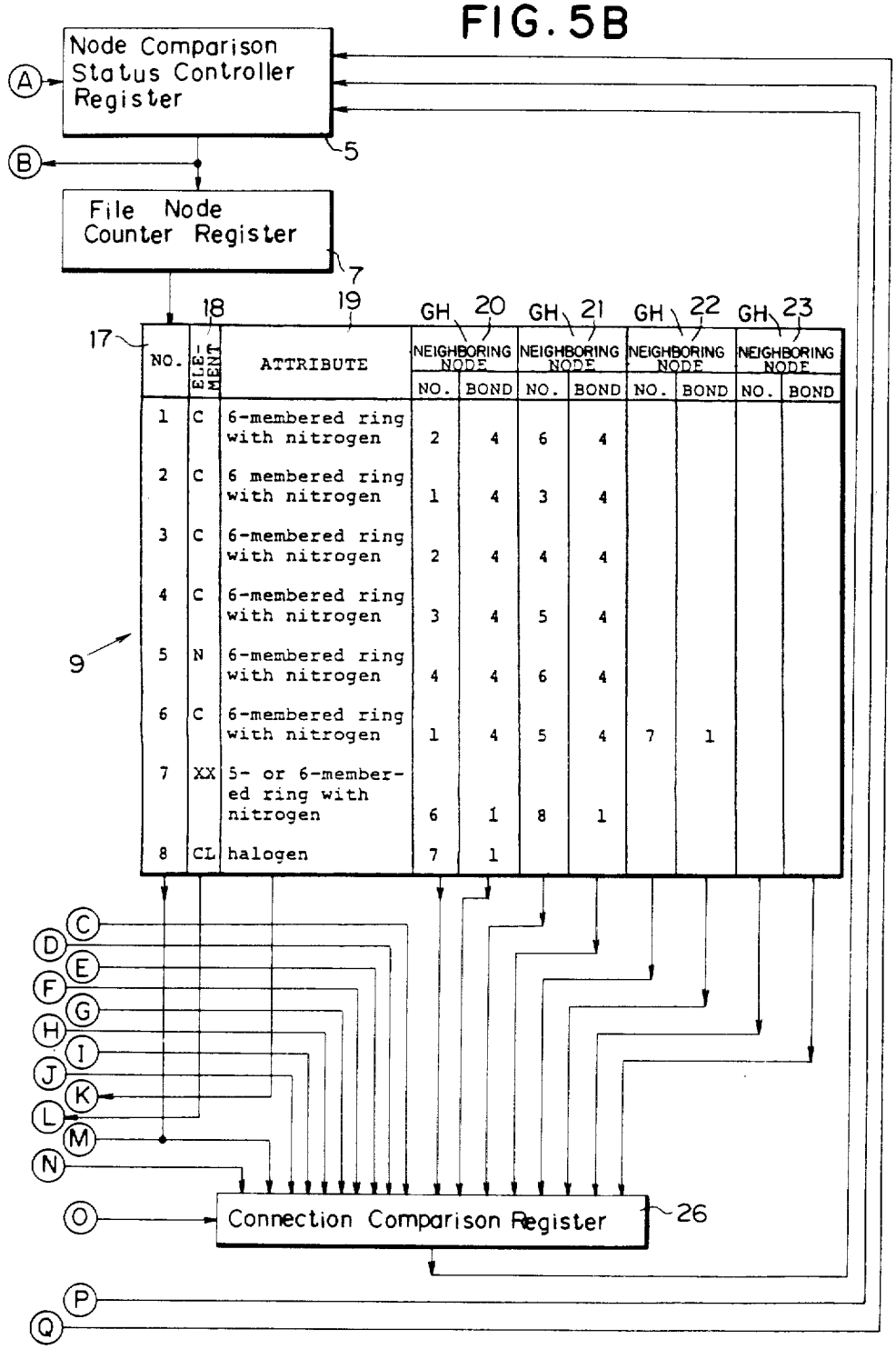

An apparatus which would operate in accordance with our search process is illustrated in FIGS. 5A-5B. First, the query structure is input by the graphic structure input device 1, and converted into a connection table. The connection table data is fed to each component register of the connection table register 8. Usually there is more than one structure in a file, and thus the search controller 3 reads a connection table and set data to each component register of the connection table register 9. The count of the file connection table is incremented whenever a new connection table is read. The comparison of a query structure and a file structure is controlled by the node comparison status controller register.

There are several methods described elsewhere for matching the connecting nodes. Although we chose the connectivity stack method here, it is certainly not the sole method to achieve the goal.

The specific search process conducted by the node comparison status controller based on the connectivity stack method is illustrated in FIG. 1.

Here nodes of the query structure (hereafter called query nodes) are numbered by i. By definition, $0<i<=m$, where m is the count of the query nodes. Similarly, nodes of a candidate structure in the file (hereafter called file nodes) are numbered by j. Also by definition, $0<j<=n$, where n is the number of file nodes. A vector P(i) is defined to store the number of a file node which matches the query node i. Another vector M(j) is defined to mark if the file node j is already matched with a query node. If it is, its value is 1. Otherwise it is 0. Since a generic file node may be matched with multiple query nodes, the M(j) value of a generic file node is kept 0. An examination of a file structure against a query structure is conducted by comparing every query node ($0<i<=m$) with every file node ($0<j<=n$), except those file nodes already matched with query nodes, for which M(J) equals 1.

The match of a query node and a file node is examined by comparing their attributes read to the attribute comparison register 24, elements where no generic nodes are involved read to the element comparison register 25, connections with nodes already matched read to the connection comparison register 26, and other conditions, if necessary. It should be noted that by only using attributes, a match can be examined between a generic node and a specific (single) node. The process is illustrated in FIG. 2.

Figure 3:
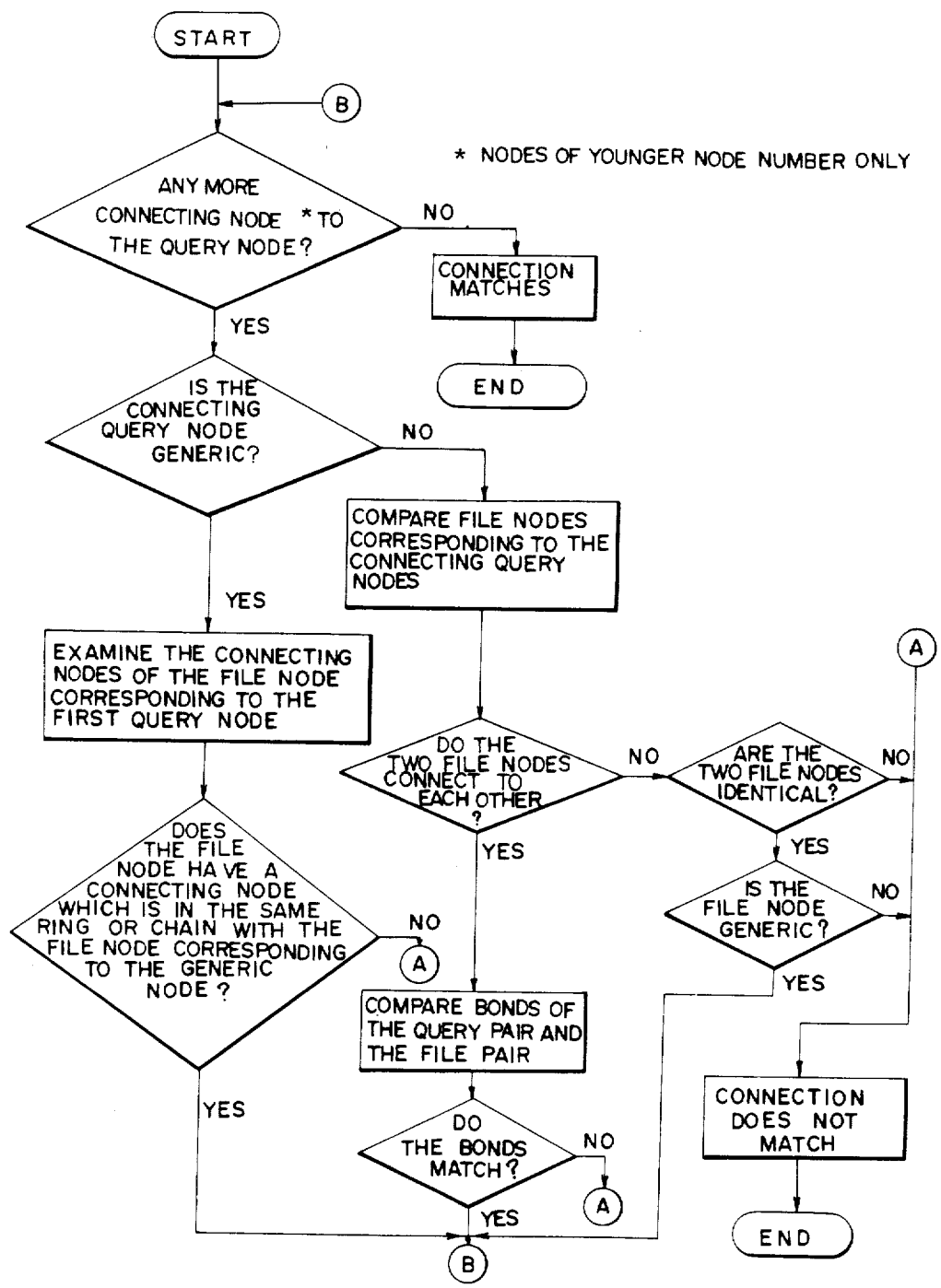
FIG. 3 illustrates a possible process of examining matches of connections around a query node and those around the corresponding file node.

The connections of a query node and those of a file node with those nodes already matched may be compared as illustrated in FIG. 3 by reading the connection data from the component register 10 to 16 of the query connection table register 8 for a particular query node, and the component registers 17 to 23 of the file connection table register 9 for a particular file node. If the query node A has a connection with a query node B already matched with a file node Y, then the file node X, which is now compared with the query node A, must have a connection with the file node Y. In addition, the bond type between X and Y must be the same with that of A and B. If the file node X is generic, i.e., can be matched with multiple query nodes, there is a chance that both A and B matches X. Then, the connection between A and B need not be examined as long as both A and B belong to the same ring or chain. If a connecting query node B is generic, a connecting file node need not be necessarily Y, which was matched with B. If a connecting file node of X, which is Z, is found to be in the same ring or chain, it is determined that the connection is matched.

Figure 2:
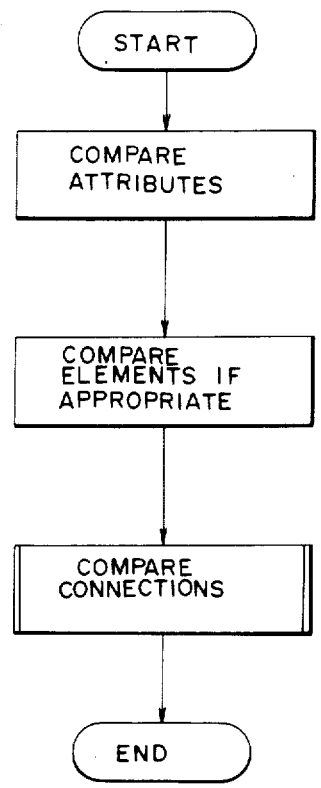
FIG. 2 illustrates a possible process of examining a match of a query node with the corresponding file node.
Figure 4:
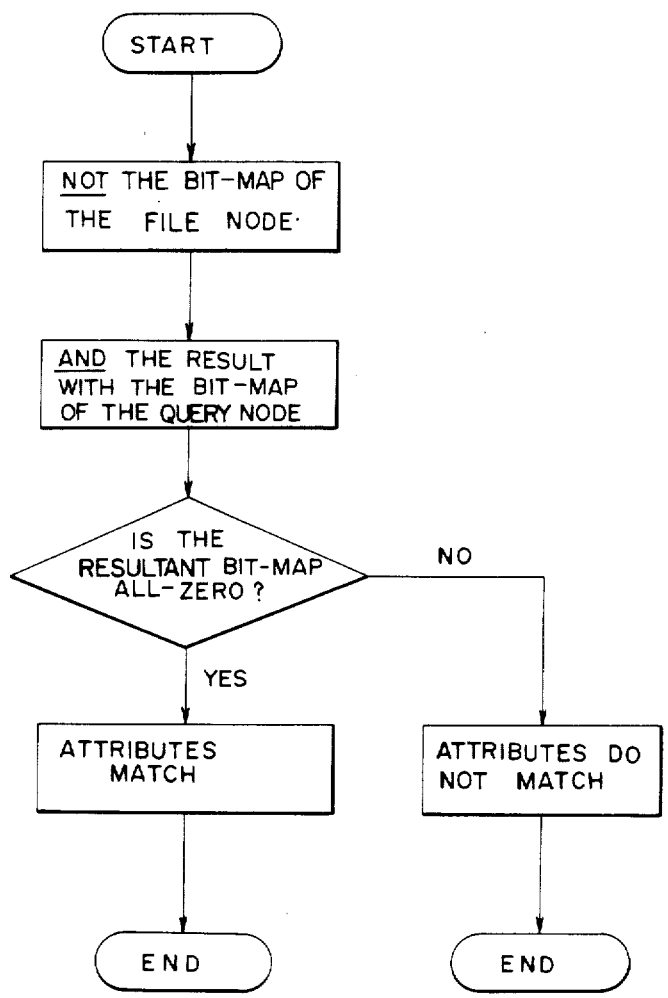
FIG. 4 illustrates a possible process of examining matches of attributes between a query node and the corresponding file node.

Attributes of a query structure and a stored structure mentioned in FIG. 2 may be compared by the steps illustrated in FIG. 4. A series of logical operations are applied as described earlier.

Although the steps described using the FIGS. 1, 2, 3, and 4 illustrate a typical search procedure of this invention, certainly it is not the sole method to achieve the goal. Any procedure which use the chemical structure attributes defined in this invention is a valid alternative.

(3) Step-by-Step Illustration

A step-by-step illustration is given in Table 5, using the example Structures 1 and 2, and Tables 1, 2, 3 and 4. As described in Table 5, this method develops a vector with the node numbers of the query structure as components, and assign the nodes of the stored structure one by one, comparing the connection with other nodes.

TABLE 5

| | MODE OF QUERY | A | B | C | D | E | F | G | CON-NECT | MATCH | ELE-MENT | ATTRIB-UTE | BOND |
|---|---|---|---|---|---|---|---|---|---|---|---|---|---|
| STEP | 1 | 1 | | | | | | | 1-A | O | * | O | |
| | 2 | 1 | 2 | | | | | | 2-B | X | O | X | |
| | . | | | | | | | | | | | | |
| | 8 | 1 | 8 | | | | | | 8-B | X | X | | |
| | 9 | 2 | | | | | | | 2-A | O | * | O | |
| | 10 | 2 | 1 | | | | | | 1-B | X | O | X | |
| | . | | | | | | | | | | | | |
| | 39 | 6 | | | | | | | 6-A | O | * | O | |
| | 40 | 6 | 1 | | | | | | 1-B | X | O | X | |
| | . | | | | | | | | | | | | |
| | 46 | 6 | 7 | | | | | | 7-B | O | ** | O | O |
| | 52 | 6 | 7 | 7 | | | | | 7-C | O | ** | O | O*** |
| | . | | | | | | | | | | | | |
| | 72 | 6 | 7 | 7 | 7 | 7 | 7 | 7 | 7-G | X | ** | X | |
| | 73 | 6 | 7 | 7 | 7 | 7 | 7 | 8 | 8-G | O | O | O | O |
| | 47 | 6 | 7 | 1 | | | | | 1-C | X | O | X | |

*Element is not examined for the generic node A
**Element is not examined for the generic node 7
***Presence of connection assumed between nodes belonging to a same generic node First, the node 1 of the stored structure is matched with the node A of the query structure by their attributes. The element value is not examined since the node A is generic. No connection is examined for the first node. Then, by comparing the node 2 and node B, one finds that their attributes do not match (the node B has a 5-membered ring while the node 2 has a 6-membered ring), although the element is the same. By exchanging the node 2 for the rest of the nodes of the stored structure, no matches are found at last at the step 8. Then one concludes that the initial assignment of the node 1 and the node A is irrelevant. Thus, one begins comparing the node 2 with the node A instead. The successful match is found when the node 6 is assigned to the node A, and the node 7 is compared with the node B. Since the node 7 is generic, only the attribute is examined. The attribute of the node 7 tells it has a 5- or 6-membered ring with oxygen atoms, which fulfills the condition of the node B. Since the node B is connected to the node A, it is necessary for the node 7 to be connected to the corresponding node 6. This requirement is also fulfilled fortunately. Since the bond value of those two connections are the same, that is, a single bond, the match of the node 7 and B are confirmed.

Then, the node C, D, and E of the query structure are all matched with the node 7. The match is confirmed by the fact that node C, D, and E are in the same ring system, because the generic node 7 must be a single ring system. Duplicate matches are possible, since the generic node 7 is considered to consist of multiple nodes. Finally, the node 8 matches with the node G in every respect, it is concluded that the stored structure 1 matches the query structure 2.

(4) Explanation of the Example

As is described above, by using the expanded connection tables and the attribute tables, the matches of specifically defined nodes and generic nodes are easily examined, and thus the matches of the query and stored structures containing both specific and generic nodes are determined. Ordinary electronic computers are easily programmed and conduct the search.

In the above example, the comparison is made under the requirement that a query structure is either identical with or imbedded in the stored structure. This type of search is called the sub-structure searching and widely used today on specific (not generic) substance databases. But the application of this invention is not limited to sub-structure searching but to the exact matching of structures or such searches where the requirement is that a stored structure should be embedded in the query structure.

Although only the ring attribute was described in detail in the above example, the chain attribute is also important. Chains are often expressed generically as C3–C5. When a node of a stored structure is C3–C5 and a node of a query structure is C4–C7, attributes of each nodes are expressed as in Table 6.

TABLE 6

|  | CHAIN LENGTH ATTRIBUTE | |
|---|---|---|
|  | MINIMUM | MAXIMUM |
|  | 1 2 3 4 5 6 7 8 | 1 2 3 4 5 6 7 8 |
| C3–C5 in stored structure | 1 1 1 1 1 0 0 0 | 0 0 1 1 1 1 1 1 |
| C4–C7 in query structure | 1 1 1 1 0 0 0 0 | 0 0 0 0 0 0 1 1 |

For the stored structure node, the attribute bit-map is the result of a logical OR operation of the attributes of C3, C4, and C5. On the other hand the attribute of the query node is the result of an AND combination of the attributes of C4, C5, C6, and C7. In this example, the node of the stored structure fulfill the attribute requirement of the query node, and the match is found.

Since this invention uses the extended connection table and the attribute table, the representation is compact. It requires much less computer storage than the method using whole sets of structures derived from a generic structure as described in the method A. Since this invention is based on traditional connection tables, the search system can be developed based on structure graphics. Thus, a searcher can build a query chemical structure image familiar to chemists on a graphic terminal and conduct a search using it. There is no need to learn complex coding rules as described in the method B.

This invention breaks a generic expression down to chemically-significant units and represents them by a finit number of attribute position on a bit-map. This allows one to find a match between non-identical expression such as a C3–C5 alkyl, an a C4–C7 alkyl, or a nitrogen-containing ring and a six-membered heterocycle. Since these attributes are generated for both the specifically-defined nodes and generic nodes, the comparison between those two types of nodes is easy.

Since it is usually easy to generate the attributes algorithmically from the normal generic expression as well as the specific expression, the invented method is easily implemented on a computer. It is important, too, that the invented method is compatible with the currently available specific structure search system using the connection tables so that the mixed handling of both generic structure and specific structure data is possible.

As a conclusion, this invention is particularlly useful in storing and retrieving complex chemical structures using a computer.

This invention is intended to be used in an information storage and retrieval system, specifically in a chemical and chemical structure information storage and retrieval system. This invention is specifically intended to provide an effective way to store and search complex chemical structure data, especially those chemical structure expression widely known as "generic" chemical structures, on a computer.

We claim:

1. A method of storing chemical structure data in a storage device and searching said chemical structure data using a query chemical structure by examining the match or analogy between the said query structure with the structure data stored, which comprises:

assigning numbers to each chemical unit, which can be either an atom of a specific or generic element, or a generic group of atoms, of each structure to be stored, and storing the numbers of chemical units to which the said chemical unit is chemically connected in a connection table, and storing the attribute data, which describe the chemical characteristics of the said chemical unit, in an attribute table;

then assigning numbers to each chemical unit, which can be either an atom of a specific or generic element, or a generic group of atoms, of the query chemical structure to be used to search the stored chemical structure data, and storing the numbers of chemical units to which the said chemical unit is chemically connected in a connection table, and storing the attribute data, which describe the chemical characteristics of the said chemical unit, in an attribute table, and then examining the match or analogy of the query structure and each stored chemical structure by comparing chemical units of the query chemical structure with the chemical units of the stored chemical structure by matching the attributes of the chemical unit of the stored chemical structure and the attributes of the corresponding chemical units of the query structure according to a mathematical condition defined in advance, either with or without matching the specific or generic element type of the chemical unit of the stored chemical structure and the specific or generic element type of the chemical unit of the query chemical structure.

2. The method claimed in claim 1, wherein said attribute table consists at least of attributes describing ring characteristics of chemical structures.

3. The method claimed in claim 1, wherein said attribute table is formed of an attribute vector, each column of which represents specified chemical characteristics of chemical structures, and wherein the existence or absence of the specified chemical characteristics is expressed by the existence or absence of a predefined value in the column which specifies the chemical characteristics, or is alternatively expressed by the absence or existence of a predefined value in the column which specifies the said chemical characteristics; and wherein said mathematical condition is the result of a series of logical operations conducted between a vector or vectors of a query chemical structure and a vector or vectors of a stored chemical structure.

4. The method claimed in claim 3, wherein said attribute vectors consist at least of a vector or vectors describing ring characteristics of chemical structures and a vector or vectors describing chain characteristics of chemical structures.

5. The method claimed in claim 4, wherein said logical operations are conducted using electronic computers or electronic data processors.

* * * * *